United States Patent [19]

Levin

[11] Patent Number: 6,001,120
[45] Date of Patent: Dec. 14, 1999

[54] UNIVERSAL DISSECTOR

[76] Inventor: John M. Levin, 412 Fairview Rd., Narberth, Pa. 19072

[21] Appl. No.: 08/524,497

[22] Filed: Sep. 7, 1995

[51] Int. Cl.[6] .................................................. A61B 17/28
[52] U.S. Cl. ......................... 606/207; 606/205; 606/174; 606/189
[58] Field of Search ................................... 606/189, 190, 606/207, 205, 174, 158, 208, 119; 600/210

[56] References Cited

U.S. PATENT DOCUMENTS

| | | | |
|---|---|---|---|
| 2,111,161 | 3/1938 | Wilson | 606/207 |
| 5,019,092 | 5/1991 | Klintmaln | 606/207 |
| 5,059,198 | 10/1991 | Gimpelson | 606/207 |

OTHER PUBLICATIONS

1980 American Hospital Supply Corp. American V. Mueller Division.

*Primary Examiner*—Michael Powell Buiz
*Assistant Examiner*—Kevin Truong
*Attorney, Agent, or Firm*—Caesar, Rivise, Bernstein, Cohen & Pokotilow, Ltd

[57] ABSTRACT

A surgical dissector has two sets of dissecting jaws with serrated inner surfaces to firmly grasp and dissect tissue. The second set of jaws projects transversely from the first set of jaws. Both sets of jaws are curved, and in one alternative, curvature of the second set of jaws is in a direction opposite to the curvature of the first set of jaws, while in the second alternative, the curvature of the second set of jaws is in the same direction as the curvature of the first set of jaws. In a first embodiment, for use during laparoscopic surgery, the dissector is positioned within a trocar for insertion into the body. In a second embodiment, for use during open surgery, a forceps type of dissector is disclosed.

36 Claims, 3 Drawing Sheets

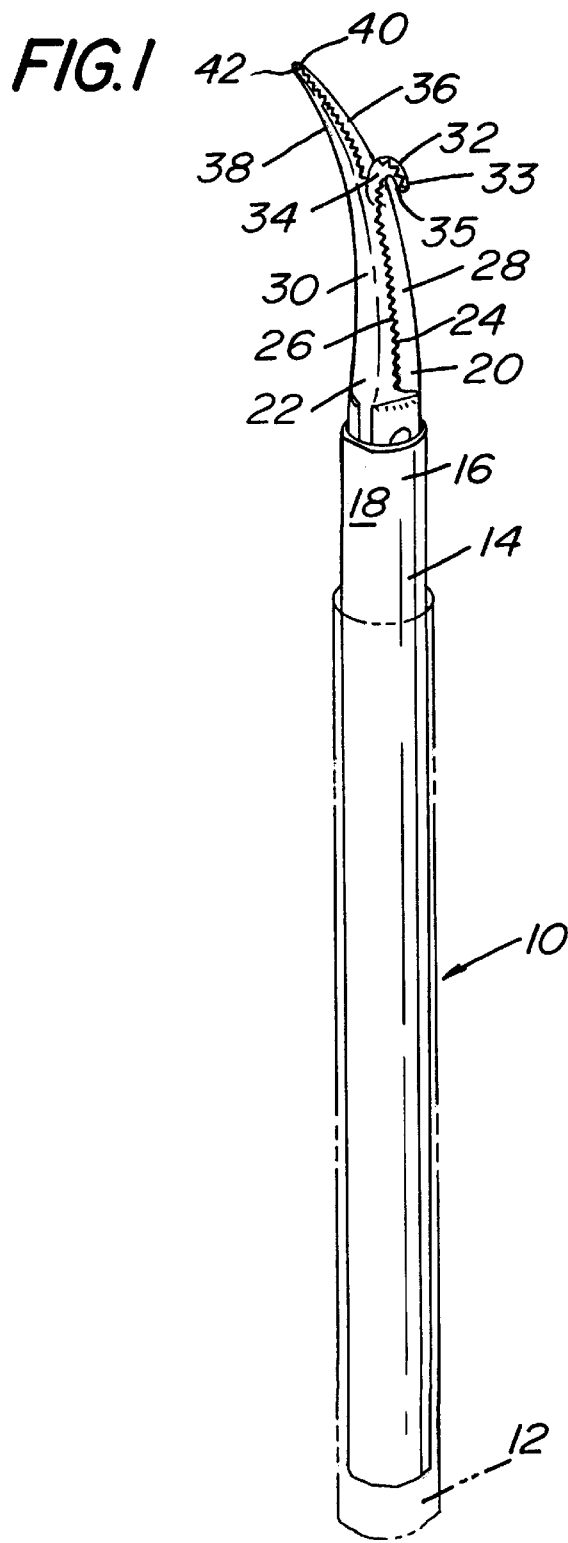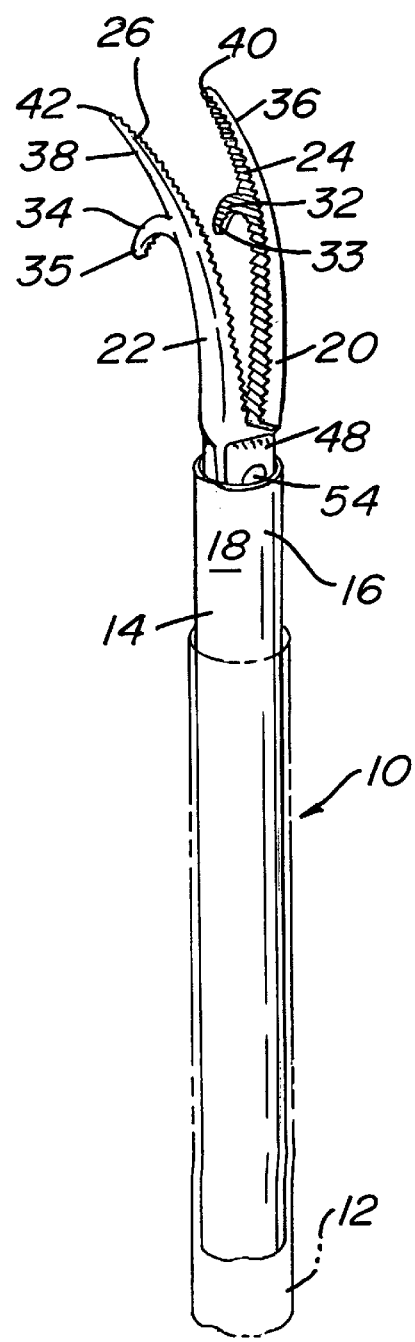

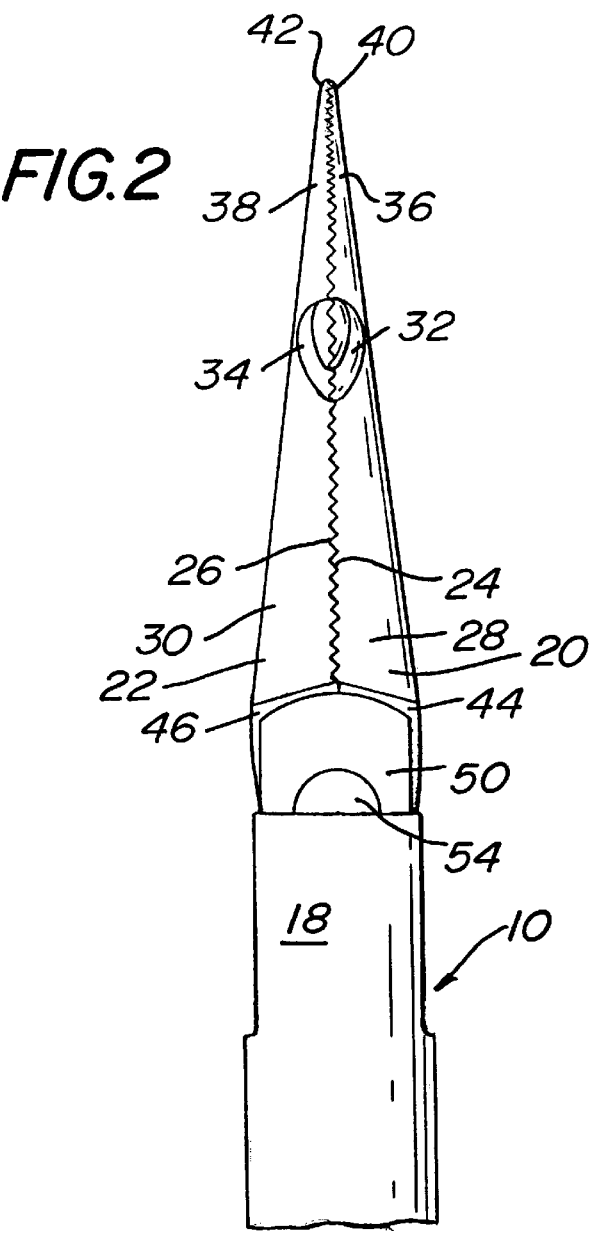
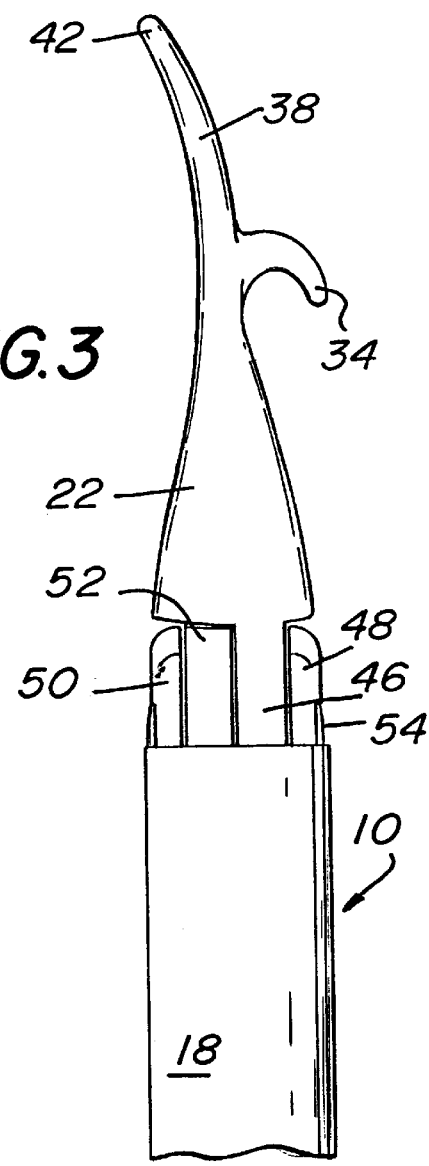
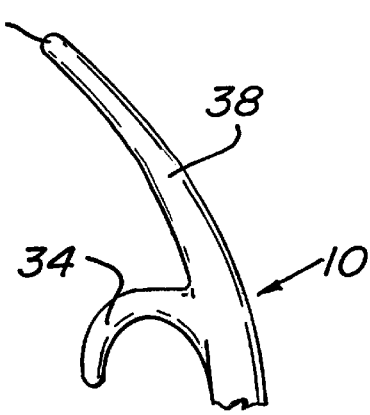

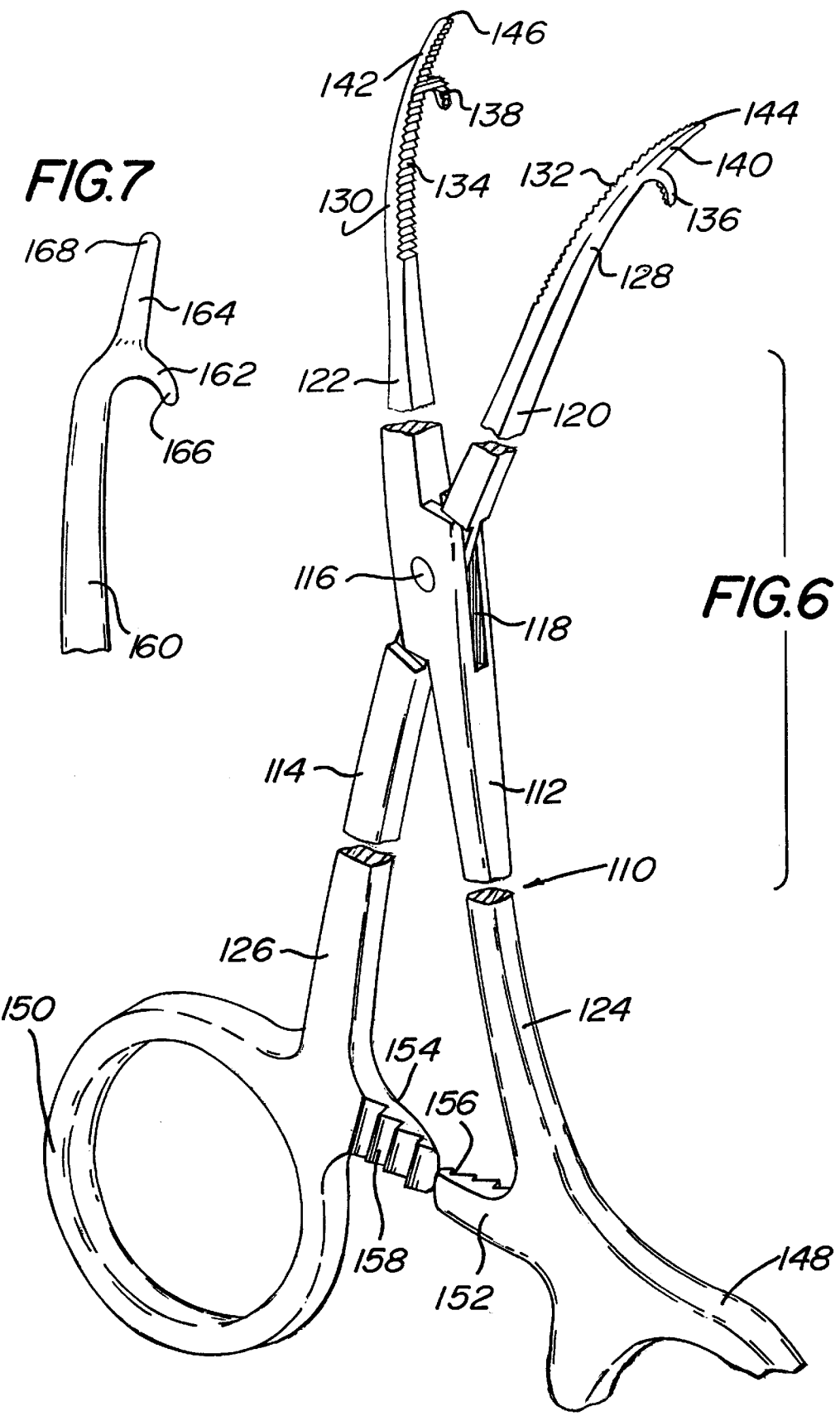

6,001,120

UNIVERSAL DISSECTOR

BACKGROUND OF THE INVENTION

Various types of dissectors are known and in use. U.S. Pat. No. 2,617,208 (Weiland) discloses an eviscerating tool having an upwardly extending projection and a downwardly extending projection.

U.S. Pat. No. 3,994,301 (Agris) discloses a submammory dissector whose head or tip extends at an acute angle to the longitudinal axis of the dissector and has a downward projection contiguous with a dissecting notch.

Another dissector, known as the Maryland dissector, uses a set of jaws with curved dissecting ends.

However, the prior art does not disclose a dissector for laparoscopic or open surgery with two sets of curved dissecting jaws, with the second set of curve dissecting jaws extending transversely from the first set of curved dissecting jaws in a direction opposed to the curvature of the first set of dissecting jaws or, in another embodiment, in the same direction of the curvature of the first dissecting jaws.

OBJECTS OF THE INVENTION

Accordingly, it is the general object of the instant invention to provide a dissector which improves upon existing dissectors.

It is a further object of the instant invention to provide a dissector with a plurality of sets of dissecting jaws.

It is yet a further object of the instant invention to provide a dissector which can reach hard to access parts of the body during surgery.

It is still a further object of the instant invention to provide a dissector with a first and a second set of dissecting jaws wherein the second set of dissecting jaws projects transversely to the first set of dissecting jaws.

It is still yet a further object of the instant invention to provide a dissector with a first and a second set of curved dissecting jaws wherein the curvature of the second set of curved dissecting jaws is in a direction opposite to the curvature of the first set of curved dissecting jaws.

It is another object of the instant invention to provide a dissector with a first and a second set of dissecting jaws wherein the curvature of the second set of dissecting jaws is in the same direction as the curvature of the first set of dissecting jaws.

It is still another object of the instant invention to provide a dissector with a plurality of sets of dissecting jaws for use during laparoscopic surgery.

It is still yet another object of the instant invention to provide a dissector with a plurality of sets of dissecting jaws for use during open surgery.

SUMMARY OF THE INVENTION

These and other objects of the instant invention are achieved by providing a dissector with the first set of curved dissecting jaws and a second set of curved dissecting jaws extending transversely from the first set of dissecting jaws. The second set of dissecting jaws may have a curvature in the same direction as the curvature of the first set of dissecting jaws or alternatively it may have a curvature in a direction opposite to the curvature of the first set of dissecting jaws. In the first embodiment of this invention, the dissector is designed and sized for laparoscopic surgery. In a second embodiment of this invention, the dissector is designed and sized for open surgery.

DESCRIPTION OF THE DRAWINGS

Other objects and many of the intended advantages of this invention will be readily appreciated when the same becomes better understood by reference to the following detailed description, when considered in connection with the accompanying drawings, wherein:

FIG. 1 is an isometric view of the first embodiment of the dissector for use in laparoscopic surgery;

FIG. 2 is a front view of the dissector;

FIG. 3 is a side view of the dissector;

FIG. 4 is an isometric view of an alternative design of the dissector, wherein the second set of curved dissecting jaws has a curvature in the same direction as the curvature of the first set of curved dissecting jaws;

FIG. 5 is a side view of the alternative dissector of FIG. 4;

FIG. 6 is a broken away isometric view of a second embodiment of the dissector for use in open surgery; and FIG. 7 is a side view of the curved end of an alternative design of the second embodiment of the dissector with the second set of jaws projecting from the curved end of the first set of jaws.

DETAIL DESCRIPTION OF THE PREFERRED EMBODIMENTS

Referring now in greater detail to the various Figures of the drawings, wherein like reference characters refer to like parts, there is shown in FIGS. 1–5 the dissector 10 structured in accordance with this invention. As can be seen in the Figs., the dissector 10, which is used for laparoscopic surgery, is inserted within a trocar 12. The dissector 10 comprises an inner cylindrical body 14 having a distal end 16 and an outer surface 18. Extending from the distal end 16 is a first set of curved jaws, comprising a first dissector jaw 20 and a second dissector jaw 22. The first jaw 20 and the second jaw 22 have inner serrated surfaces 24 and 26 respectively. As can be seen in FIG. 1 the serrated inner surfaces 24 and 26 intermesh when the jaws are closed. The jaws 20 and 22 also have convex outer surfaces 28 and 30 respectively. The dissector 10 also has a second set of curved jaws, comprising a third jaw 32 and a fourth jaw 34, which project transversely from the convex outer surfaces 28 and 30, respectively. The jaws 20 and 22 have distal ends 36 and 38 and blunt tips 40 and 42 respectively which terminate the distal ends 36 and 38. Likewise, the second set of jaws 32 and 34 have blunt tips 33 and 35, respectively.

FIGS. 1, 2, and 3 show a first alternative structure of the dissector 10 in which the second set of jaws, jaws 32 and 34 have a curvature in the direction opposite to the curvature of the first set of jaws 20 and 22. FIGS. 4 and 5 show a second alternative structure of the laparoscopic dissector 10 in which the second set of jaws 32 and 34 have a curvature in the same direction as the curvature of the first set of jaws 20 and 22.

The jaws 20 and 22 have proximal ends 44 and 46. The dissector 10 also comprises blocks 48 and 50 and a spacer 52, respectively (FIGS. 2 & 3), which are connected at said distal ends. The dissector 10 also has a pivot pin 54 to which the jaws 20 and 22 are pivotally connected. The pivot pin 54 extends through the blocks 48 and 50 and the spacer 52.

Mechanisms for opening and closing the jaws of the laparoscopic dissectors of FIGS. 1–5 by the surgeon are well known to those skilled in the art. Therefore, they are not shown and discussion of these mechanisms is not required. Any standard such mechanism can be used with this invention.

A second embodiment of the dissector of this invention is shown in FIGS. 6 and 7. Whereas the previous embodiment comprises a dissector used for laparoscopic surgery, this second embodiment is primarily for use in open surgery. It comprises a forceps type of dissector 110 having a first arm 112, a second arm 114 and a pivot pin 116 which pivotally connects the first and the second arms 112 and 114. The first and the second arms 112 and 114 have slots 118 which provide room for the jaws to be opened and closed by rotating them about the pivot pin 116.

The first arm 112 and the second arm 114 also have distal sections 122 and 120 and proximal sections 124 and 126, respectively. The distal sections 120 and 122 comprise a first set of jaws, with a curved first jaw 128 and a curved second jaw 130 which have inner serrated surfaces 132 and 134, distal ends 140 and 142 and blunt tips 144 and 146 respectively at the ends of the jaws. The distal sections 120 and 122 also include a second set of jaws, a third jaw 136 and a fourth jaw 138, respectively, which project transversely from the curved first jaw 128 and the curved second jaw 130.

The proximal sections 124 and 126 further include finger rings 148 and 150 and projections 152 and 154, respectively. The projections 152 and 154 have ratcheted inner surfaces 156 and 158. Thus, in open surgery, this forceps type of dissector 110 is held and manipulated by the surgeon by placing his or her fingers in the finger rings 148 and 150 and the opening and closing of the curved jaws 128 and 130 are controlled by the movement of the fingers of the surgeons. When tissue is grasped, the ratcheted surfaces 156 and 158 intermesh holding the jaws in position for better control by the surgeon.

It is should be noted here, that the basic structure and shape of the jaws 128, 130, 136 and 138 of this second embodiment is the same as the jaws 20, 22, 32 and 34 of the first embodiment of FIG. 4, with the second set of jaws 136 and 138 being curved in the same direction as the first set of jaws 128 and 130, except that in the first embodiment for the laparoscopic dissector, the size and scale of the dissector jaws may be smaller than the jaws of the second embodiment which is used for open surgery. Of course, the dissector 110 can have the second set of jaws which a curvature in a direction opposite to the first set of jaws as is shown in FIG. 1 of the dissector 10.

FIG. 7 shows an additional alternative structure of the second embodiment wherein the first and second jaws 160 each have a curved end 162 terminating in a blunt tip 166. The dissector also includes a second set of jaws 164 with a blunt tips 168 which project from the curved ends 162.

It should be noted that, in the various embodiments and alternatives described above, the ends of the jaws are blunt to prevent damage to tissues as the surgeon uses the dissector to separate or remove tissues or other body matter. It should also be emphasized that all the alternatives shown in both embodiments are available and can be used for either embodiment.

The dissectors are specifically designed to assist the surgeon during certain procedures. For example, the first set of jaws are capable of dissecting the forward end of various body parts such as the cystic duct and the artery which connects to the gallbladder and the second set of jaws is capable of encircling the cystic duct and artery to clean off the rear end thereof. Generally, the areolar tissue (thinned fascial tissue) that surrounds and covers the artery is dissected. The curved second set of jaws extends away from the liver during use of the dissector thereby precluding the leading edge of the first set of jaws from possibly injuring the liver when the second set of jaws is being employed.

A dissector has been described which has two sets of curved jaws, a first set and a second set which is connected to and extends transversely from the first set of jaws. The positioning and shape of the jaws is designed to assist the surgeon in various types of dissecting operations. The dissector allows the surgeon to perform various types of dissecting operations with a single instrument and is specifically shaped and structured to provide access to the surgeon for dissecting tissue or other body matter in hard to reach locations. Without further elaboration, the foregoing will so fully illustrate my invention that others may, by applying current or future knowledge, readily adapt the same for use under the various conditions of service.

I claim:

1. A dissector comprising a first set of dissecting jaws and a second set of dissecting jaws, said first set of dissecting jaws comprising a first and second jaw, each of said first and second jaws having an outer surface and a distal end terminating in a blunt tip for dissecting tissue, and said second set of dissecting jaws comprising a third and a fourth jaw, said third jaw being connected to, and projecting from said outer surface of said first jaw at a location proximally of the blunt tip of said first jaw and said fourth jaw being connected to, and projecting from said outer surface of said second jaw at a location proximally of the blunt tip of said second jaw, said dissector further comprising pivot means for connecting said first and second jaws.

2. The dissector of claim 1 wherein said first set of dissecting jaws and said second set of dissecting jaws are curved.

3. The dissector of claim 2 wherein said second set of dissecting jaws has a curvature in the same direction as the curvature of said first set of dissecting jaws.

4. The dissector of claim 3 wherein said first and second jaws have proximal and distal ends and said third and fourth jaws are connected to said first and second jaws respectively at said distal ends.

5. The dissector of claim 4 wherein said first, second, third and fourth jaws have serrated inner surfaces.

6. The dissector of claim 2 wherein said first and second jaws have proximal and distal ends and said third and fourth jaws are connected to said first a second jaws respectively at said distal ends.

7. The dissector of claim 6 wherein said first, second, third and fourth jaws have serrated inner surfaces.

8. The dissector of claim 2 wherein said second set of dissecting jaws has a curvature in a direction which is opposite to the curvature of said first set of dissecting jaws.

9. The dissector of claim 2 wherein said first and second jaws each comprises a straight segment and a curved distal end attached to said straight segment and said third and fourth jaws are connected to, and project from, said curved distal ends.

10. The dissector of claim 1 wherein said first, second, third and fourth jaws have serrated inner surfaces.

11. The dissector of claim 10 wherein said first set of dissecting jaws and said second set of dissecting jaws are curved.

12. The dissector of claim 11 wherein said second set of dissecting jaws has a curvature in the same direction as the curvature of said first set of dissecting jaws.

13. The dissector of claim 11 wherein said second set of dissecting jaws has a curvature in a direction which is opposite to the curvature of said first set of dissecting jaws.

14. A dissector for use in open surgery comprising a first and a second arm, each arm having a distal end and a proximal end with a first set of jaws comprising a first jaw and a second jaw at said distal ends of said first and second arms, respectively, each of said first and second jaws having an outer surface and a distal end terminating in a blunt tip for dissecting tissue, said dissector further comprising a second set of jaws comprising a third jaw and a fourth jaw connected to, and projecting transversely from, said outer surfaces of said first and second jaws respectively, at locations proximally of the blunt tip of said first and second jaws, and means for pivotally connecting first and second arms.

15. The dissector of claim 14 further comprising a first and a second finger loop at said proximal ends of said first and said second arms, respectively.

16. The dissector of claim 15 wherein said first set of dissecting jaws and said second set of dissecting jaws are curved.

17. The dissector of claim 16 wherein said second set of dissecting jaws have a curvature in the same direction as the curvature of said first set of dissecting jaws.

18. The dissector of claim 16 wherein said second set of dissecting jaws has a curvature in a direction which is opposite to the curvature of the curvature of said second set.

19. The dissector of claim 15 wherein said finger loops each have a side projecting member with a ratcheted inner surface, said side projecting members intermeshing with each other to maintain said first arm at a fixed position relative to said second arm.

20. The dissector of claim 19 wherein said first set of dissecting jaws and said second set of dissecting jaws are curved.

21. The dissector of claim 20 wherein said second set of jaws has a curvature in the direction opposite to the curvature of said first set of jaws.

22. The dissector of claim 20 wherein said second set of jaws has a curvature in the same direction as the curvature of said first set of jaws.

23. The dissector of claim 14 wherein said first, second, third and fourth jaws have serrated inner surfaces.

24. The dissector of claim 14 wherein said first set of dissecting jaws and said second set of dissecting jaws are curved.

25. The dissector of claim 14 wherein said first set of jaws is curve and said second set of jaws is straight.

26. The dissector of claim 25 wherein said first, second, third and fourth jaws have serrated inner surfaces.

27. A dissector comprising a first set of curved dissecting jaws and a second set of curved dissecting jaws, said first set of dissecting jaws comprising a first and a second jaw, each of said first and second jaws having an outer surface and said second set of dissecting jaws comprising a third jaw and a fourth jaw, said third jaw being connected to, and projecting from said outer surface of said first jaw, and said fourth jaw being connected to, and projecting from said outer surface of said second jaw, said second set of dissecting jaws having a curvature in a direction which is opposite to the curvature of said first set of jaws, said dissector further comprising means for pivotally connecting said first and second jaws.

28. A dissector comprising a first set of curved dissecting jaws and a second set of curved dissecting jaws, said first set of dissecting jaws comprising a first and a second jaw, each of said first and second jaws having an and a distal end terminating in a tip for dissecting tissue and said second set of dissecting jaws comprising a third and a fourth jaw, said third jaw being connected to, and projecting from said outer surface of said first jaw at a location proximally of the tip of said first jaw and said fourth jaw being connected to, and projecting from said outer surface of said second jaw at a location proximally of the tip of said second jaw, said first, second, third and fourth jaws having serrated inner surfaces, said dissector comprising means for pivotally connecting said first and second jaws.

29. The dissector of claim 28 wherein said second set of dissecting jaws has a curvature in the same direction as the curvature of said first set of dissecting jaws.

30. The dissector of claim 28 wherein said second set of dissecting jaws has a curvature in a direction which is opposite of the curvature of said first set of dissecting jaws.

31. The dissector of claim 28 wherein said second set of dissecting jaws has a curvature in the same direction as the curvature of said first set of dissecting jaws and wherein said first and second jaws have proximal and distal ends and said third and fourth jaws are connected to said first and second jaws, respectively, at said distal ends.

32. The dissector of claim 28 wherein said first and second jaws have proximal and distal ends and said third and fourth jaws are connected to said first and second jaws, respectively, at said distal ends.

33. A dissector for use in open surgery comprising a first and a second arm, each arm having a distal end and a proximal end with a first set of curved dissecting jaws comprising a first jaw and a second jaw at said distal ends of said first and second arms respectively, each of said first and second, curved, dissecting jaws having an and a distal end terminating in a tip for dissecting tissue said dissector further comprising a second set of curved dissecting jaws comprising a third jaw and a fourth jaw connected to, and projecting transversely from, said outer surfaces of said first and second dissecting jaws at locations proximal of the tips said first and second jaws, respectively, said second set of dissecting jaws having a curvature in the same direction as the curvature of said first set of dissecting jaws, and means for pivotally connecting said first and second arms.

34. The dissector of claim 33 further comprising a first and second finger loop at said proximal ends of said first and second arms, respectively.

35. A dissector for use in open surgery comprising a first and a second arm, each arm having a distal end and a proximal end with a first set of curved dissecting jaws comprising a first jaw and a second jaw at said distal ends of said first and second arms respectively, each of said first and second, curved, dissecting jaws having an outer surface said dissector further comprising a second set of curved dissecting jaws comprising a third jaw and a fourth jaw connected to, and projecting transversely from, said outer surfaces of said first and second dissecting jaws, respectively, said second set of dissecting jaws having a curvature in a direction opposite to the curvature of said first set of dissecting jaws, further comprising a first and second finger loop at said proximal ends of said first and second arms, respectively, said finger loops each having a side projecting member with a ratcheted inner surface, said side projecting members intermeshing with each other to maintain said first arm at a fixed position relative to said second arm, and means for pivotally connecting said first and second arms.

36. The dissector of claim 35, wherein said finger loops each have a side projecting member with a ratcheted inner surface, said side projecting members intermeshing with each other to maintain said first arm in a fixed position relative to said second arm.

* * * * *